US005387951A

United States Patent [19]

Hatanaka

[11] Patent Number: 5,387,951

[45] Date of Patent: Feb. 7, 1995

[54] INTRAOCULAR LENGTH MEASURING INSTRUMENT CAPABLE OF AVOIDING ERRORS IN MEASUREMENT CAUSED BY THE MOVEMENT OF A SUBJECT'S EYE

[75] Inventor: Hideki Hatanaka, Tokyo, Japan

[73] Assignee: Kabushiki Kaisha Topcon, Tokyo, Japan

[21] Appl. No.: 62,767

[22] Filed: May 18, 1993

[30] Foreign Application Priority Data

May 19, 1992 [JP] Japan .................................. 4-125241

[51] Int. Cl.$^6$ .................................. A61B 3/10

[52] U.S. Cl. .................................. 351/205; 351/211; 351/221

[58] Field of Search ............... 351/200, 205, 206, 214, 351/211, 221; 128/665, 745

[56] References Cited

U.S. PATENT DOCUMENTS

| | | | |
|---|---|---|---|
| 4,796,989 | 1/1989 | Fukuma et al. | 351/205 |
| 5,141,302 | 8/1992 | Arai et al. | 351/205 |

*Primary Examiner*—William L. Sikes
*Assistant Examiner*—Huy Mai
*Attorney, Agent, or Firm*—Finnegan, Henderson Farabow, Garrett & Dunner

[57] ABSTRACT

An intraocular length measuring instrument according to the invention can avoid errors in measurement caused by the movement of a subject's eye, such as a blink or involuntary eye movement, and improve the accuracy of the measurement of an intraocular length of the eye. The intraocular length measuring instrument includes a pattern image projecting and receiving optical system for projecting a pattern image onto the cornea of the eye and receiving the pattern image into a two-dimensional image sensor; an interferometric system for producing interference light in such a way that measuring light is projected onto a surface of an intraocular object to be measured while reference light is projected onto a reference surface corresponding to the object surface and interference is caused between light reflected by the object surface and light reflected by the reference surface and causing a photosensor to receive the interference light and output an interference signal; a device for determining the position of the object surface by sampling interference signals output by the photosensor; a device for reading the data concerning the pattern image received by the two-dimensional image sensor at any point of time of the duration of the sampling in order to memorize the pattern image data in a memory medium; and means for determining the position of a corneal vertex from the pattern image data memorized in the memory medium.

4 Claims, 5 Drawing Sheets

INTRAOCULAR LENGTH MEASURING INSTRUMENT CAPABLE OF AVOIDING ERRORS IN MEASUREMENT CAUSED BY THE MOVEMENT OF A SUBJECT'S EYE

BACKGROUND OF THE INVENTION

1. Field of the Invention

This invention relates to an intraocular length measuring instrument in which the position of a corneal vertex is found by using an optical system relating to geometrical optics, the position of the surface of an intraocular object to be measured is found by using an interferometric system relating to physical optics, and the intraocular length between the positions of the corneal vertex and the object surface is measured.

2. Description of the Prior Art

A conventional intraocular length measuring instrument well-known in the art includes a pattern image projecting and receiving optical system and an interferometric system. In the pattern image used projecting and receiving optical system, a ring image as a pattern image is projected onto the cornea of a subject's eye and then received into a two-dimensional image sensor. In the interferometric system, a measuring beam of light is projected onto the surface of an intraocular object to be measured while a reference beam of light is projected onto a reference surface corresponding to the surface of the object, interference is then caused between the respective beams of light reflected from the object surface and the reference surface, its resultant interference light is guided to a photosensor, and an interference signal is output from the photosensor. Finally in the intraocular length measuring instrument, a corneal vertex position is found by the pattern image projecting and receiving optical system, an object surface position is found by the interferometric system, and the intraocular length between the corneal vertex and the object surface is calculated from those positions.

In this conventional instrument, the photosensor provided in the interferometric system outputs a maximum amplitude waveform and, immediately after that, data concerning the ring image received by the two-dimensional image sensor is memorized in a frame memory used as a memory medium. Then the corneal vertex position is determined from the memorized data while the position of the object surface is determined from the interference signal obtained by the interferometric system.

However, the conventional instrument has a fault in that there is a time-lag of at least 1/30 seconds or so between the ring image data for determining the corneal vertex position and the data for determining the object surface position. If the eye blinks or is involuntarily moved during this time-lag, the corresponding relationship between those data is disturbed greatly and this disadvantageously leads to an inaccurate measurement of the intraocular length.

SUMMARY OF THE INVENTION

It is therefore an object of the invention to provide an intraocular length measuring instrument capable of avoiding an error in measurement caused by the movement of a subject's eye, such as a blink or involuntary eye movement, to the utmost and improving the accuracy of the measurement of an intraocular length of the eye.

To accomplish the object, an intraocular length measuring instrument according to one embodiment of the invention is characterized by:

a pattern image projecting and receiving optical system for projecting a pattern image onto the cornea of the eye and receiving the pattern image into a two-dimensional image sensor;

an interferometric system for producing interference light in such a way that measuring light is projected onto a surface of an intraocular object to be measured while reference light is projected onto a reference surface corresponding to the object surface and interference is caused between light reflected by the object surface and light reflected by the reference surface and causing a photosensor to receive the interference light and output an interference signal;

means for determining the position of the object surface by sampling interference signals output by the photosensor;

means for reading data concerning the pattern image received by the two-dimensional image sensor when the object surface position determining means is sampling the interference signals in order to memorize the data in a memory medium; and means for determining the position of a corneal vertex from the pattern image data memorized in the memory medium.

To accomplish the object, an intraocular length measuring instrument according to the invention is characterized by:

a ring image projecting and receiving optical system for projecting a ring image onto the cornea of the eye and receiving the ring image into a two-dimensional image sensor;

an interferometric system for producing interference light in such a way that measuring light is projected onto a surface of an intraocular object to be measured while reference light is projected onto a reference surface corresponding to the object surface and interference is caused between light reflected by the object surface and light reflected by the reference surface and causing a photosensor to receive the interference light and output an interference signal;

a circuit for determining the position of the object surface from interference signals output by the photosensor;

means for reading the data concerning the ring image received by the two-dimensional image sensor at any point of time of the duration of the sampling in order to memorize the data in a memory medium; and a circuit for determining the position of a corneal vertex from the ring image data memorized in the memory medium.

According to the intraocular length measuring instrument according to the invention, the pattern image projecting and receiving optical system projects a pattern image onto the cornea of the eye and receives the pattern image into a two-dimensional image sensor. The interferometric system projects a measuring beam of light onto the surface of an intraocular object to be measured while projecting a reference beam of light onto a reference surface corresponding to the object surface, it causes interference between respective beams of light reflected from the object surface and the reference surface, it guides its resultant interference light to a photosensor, and it outputs an interference signal from the photosensor. The object surface position determining means determines the position of the object surface by sampling interference signals output by the photosensor. The reading means reads the data concerning the pattern image received by the two-dimensional image sensor at any point of time of the duration of the sampling in order to memorize the data in the memory medium. And the corneal vertex position determining means determines the position of a corneal vertex from the data concerning the pattern image memorized in the memory medium.

According to the intraocular length measuring instrument according to another embodiment of the invention, the reading means reads the data concerning the ring image received by the two-dimensional image sensor as the object surface position determining circuit determines the position of the object surface from the interference signals.

DESCRIPTION OF THE PREFERRED EMBODIMENTS

(Embodiment 1)

Figure 1:
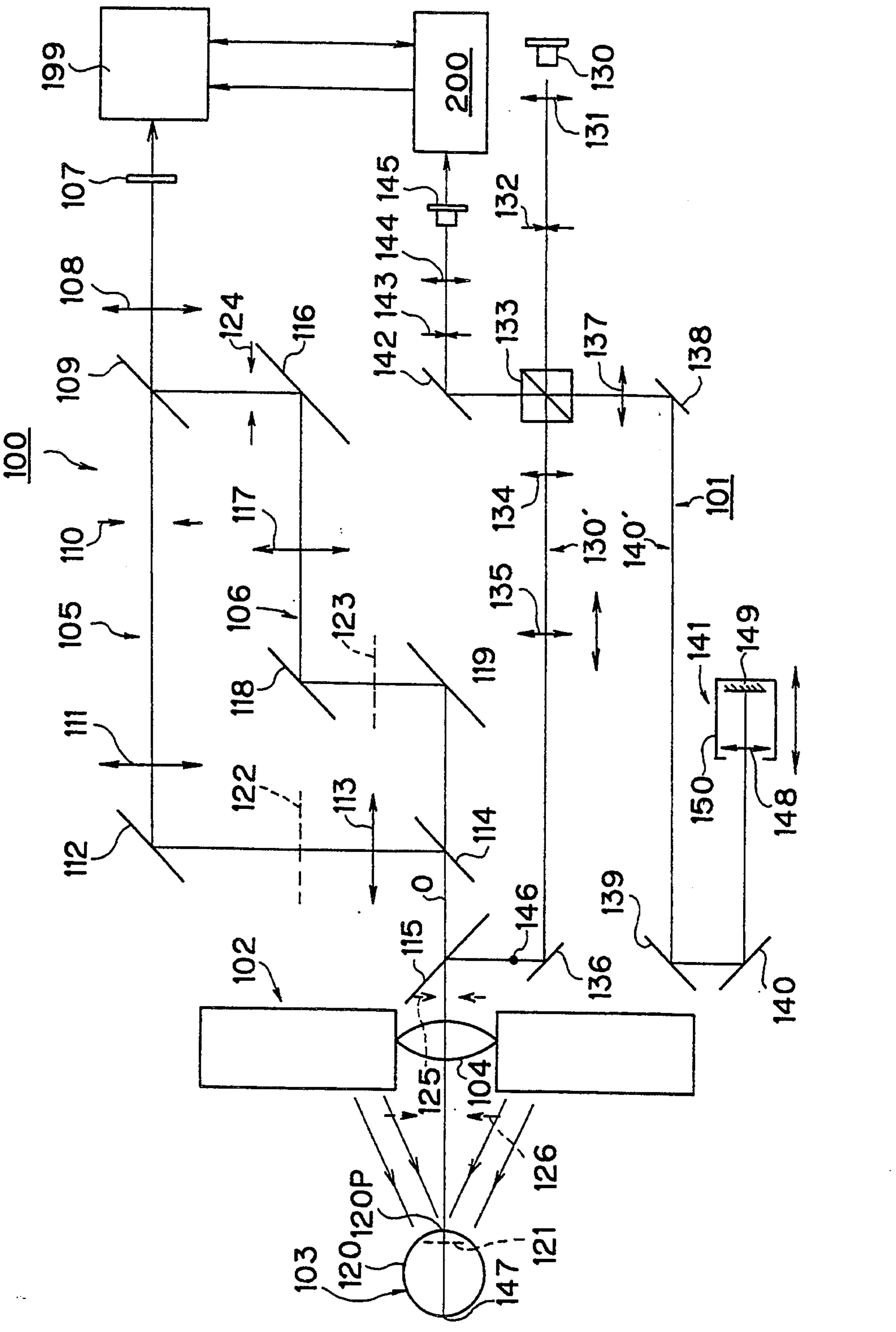
FIG. 1 is a view showing a first embodiment of an optical system of an intraocular length measuring instrument according to the invention.

Referring first to FIG. 1, the numeral 100 denotes a ring image projecting and receiving optical system used as a pattern image projecting and receiving optical system, and the numeral 101 denotes an interferometric system. The interferometric system 101 includes a laser diode 130, a lens 131, a pin hole 132, a beam splitter 133, a lens 134, a focusing lens 135, a total reflection mirror 136, a lens 137, total reflection mirrors 138, 139, and 140, a model eye unit member 141, a total reflection mirror 142, a pin hole 143, a lens 144, and a point-apertured photosensor 145. The laser diode 130 is of a short coherent length. The coherent length is, for example, approximately 0.05 mm to 0.1 mm. The wavelength is near infrared and has an effect for preventing dazzling. A laser beam emitted by the laser diode 130 is condensed to the pin hole 132 by the lens 131. The pin hole 132 serves as a second point source. Instead of the laser diode 130, an LED (light emitting diode) having a narrow spectral width may be used as a light source.

The laser beam transmitted through the pin hole 132 is split into a beam of light proceeding to the lens 184 and a beam of light proceeding to the lens 137 by the beam splitter 133. The lens 134 makes up a measuring optical path 130' together with the focusing lens 135, the total reflection mirror 136, and a dichroic mirror 115. The lens 137 makes up a reference optical path 140' together with the total reflection mirrors 138, 139, and 140, and the model eye unit member 141.

The lenses 134 and 187 serve to collimate the laser beam transmitted through the pin hole 132. The laser beam collimated by the lens 134 forms a spot by means of the focusing lens 135 at the focal point 146 thereof. This focal point 146 is conjugate to an eye fundus 147 as an object surface to be measured with respect to an objective lens 104. The laser beam forming the spot at the focal point 146 is guided to the subject's eye via the total reflection mirror 136, the dichroic mirror 115, the objective lens 104 and then forms a spot at the eye fundus 147 of the eye. Since the eye fundus 147 is conjugate to the focal point 146 with respect to the objective lens 104 here, light reflected from the eye fundus 147 can form an image at the focal point 146 even if the optical axis of the measuring instrument (i.e., optical axis 0 of the objective lens) is not coaxial to the optical axis of the eye 103.

The pin hole 143 is disposed at the focal point of the lens 134 and is conjugate to the eye fundus 147. The focusing lens 135 serves to collimate the light reflected from the eye fundus. After collimated by the focusing lens 135, the reflected light is relayed to the pin hole 143 by the lens 134 via the beam splitter 133 and the total reflection mirror 142. Since the pin hole 143 is conjugate to the pin hole 132 with respect to the reflection surface of the beam splitter 133 and the pin hole 132 is conjugate to a spotlight formed on the eye fundus 147, the reflected light from the eye fundus can be transmitted through the pin hole 143 even if the measuring instrument is not completely in alignment with respect to the eye 103.

The laser beam collimated by the lens 137 is guided to the model eye unit member 141 via the total reflection mirrors 138, 139, and 140. The model ere unit member 141 is movable so as to equalize an optical path length of the reference optical path 140' to that of the measuring optical path 130'. The model eye unit member 141 includes a lens 148, a total reflection mirror 149 as a reference surface corresponding to the intraocular object surface, and a movable case 150. To eliminate the deflection of the reflected light caused when the model eye unit member 141 is moved and deviated, the unit member 141 is made up of the lens and the mirror located at the focal point of the lens. Therefore, a single movable mirror instead of the unit member 141 may be used in principle.

The reflected light from the eye fundus and the reflected reference light are condensed to the pin hole 143. The light transmitted through the pin hole 143 is converged upon the photosensor 145 by the lens 144. When the model eye unit member 141 is moved so that the optical path difference between the reference optical path 140' and the measuring optical path 130' becomes a coherent length or so of the laser diode 130, an interference waveform is obtained. The interference waveform is sinusoidally changed in accordance with the change of the optical path length by a wavelength. When the model eye unit member 141 is moved back and forth here, the photosensor 145 consecutively outputs a maximum amplitude waveform (a peak) of the interference signal. The interference signal is input into a signal processing circuit 200 which samples the detection data concerning a peak position of the interference signal. Since the arrangement of the hardware of the signal processing circuit 200 is known, a detailed description thereof will be omitted and a description of portions different from the conventional one will be hereinafter given.

The ring image projecting and receiving optical system 100 includes a ring-shaped light source projecting portion 102 for projecting ring-shaped light onto the cornea, a first optical path 105, and a second optical path 106. The first optical path 105 includes a two-dimensional image sensor 107, an image formation lens 108, a half mirror 114, a dichroic mirror 115, and an objective lens 104. The second optical path 106 includes a total reflection mirror 116, a lens 117, total reflection mirrors 118, 119, and a diaphragm 124.

The ring-shaped light source projecting portion 102 is made up of a ring-shaped light source and a pattern plate (not shown). Instead of the illuminating light which is parallel in rays of light in meridional section as shown in this embodiment, radiant illuminating light may be projected onto the eye. When the illuminating light is projected thereonto, a ring-shaped virtual image 121 is formed on the cornea 120 of the eye 103. Wavelengths of the illuminating light of the projecting portion 102 range from 900 nm to 1000 nm here. The dichroic mirror 115 serves to transmit the illuminating light and reflect infrared rays of light which will be described hereinafter.

Figure 2:
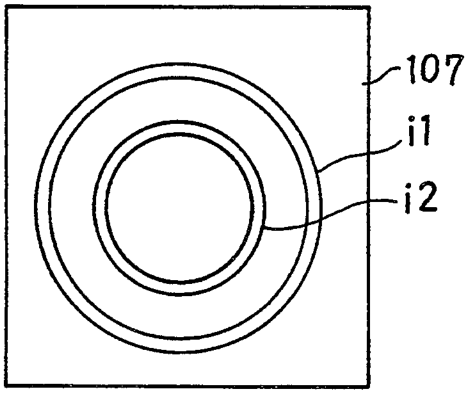
FIG. 2 is a plan view of the data concerning ring images formed on a two-dimensional image sensor shown in FIG. 1.
Figure 3:
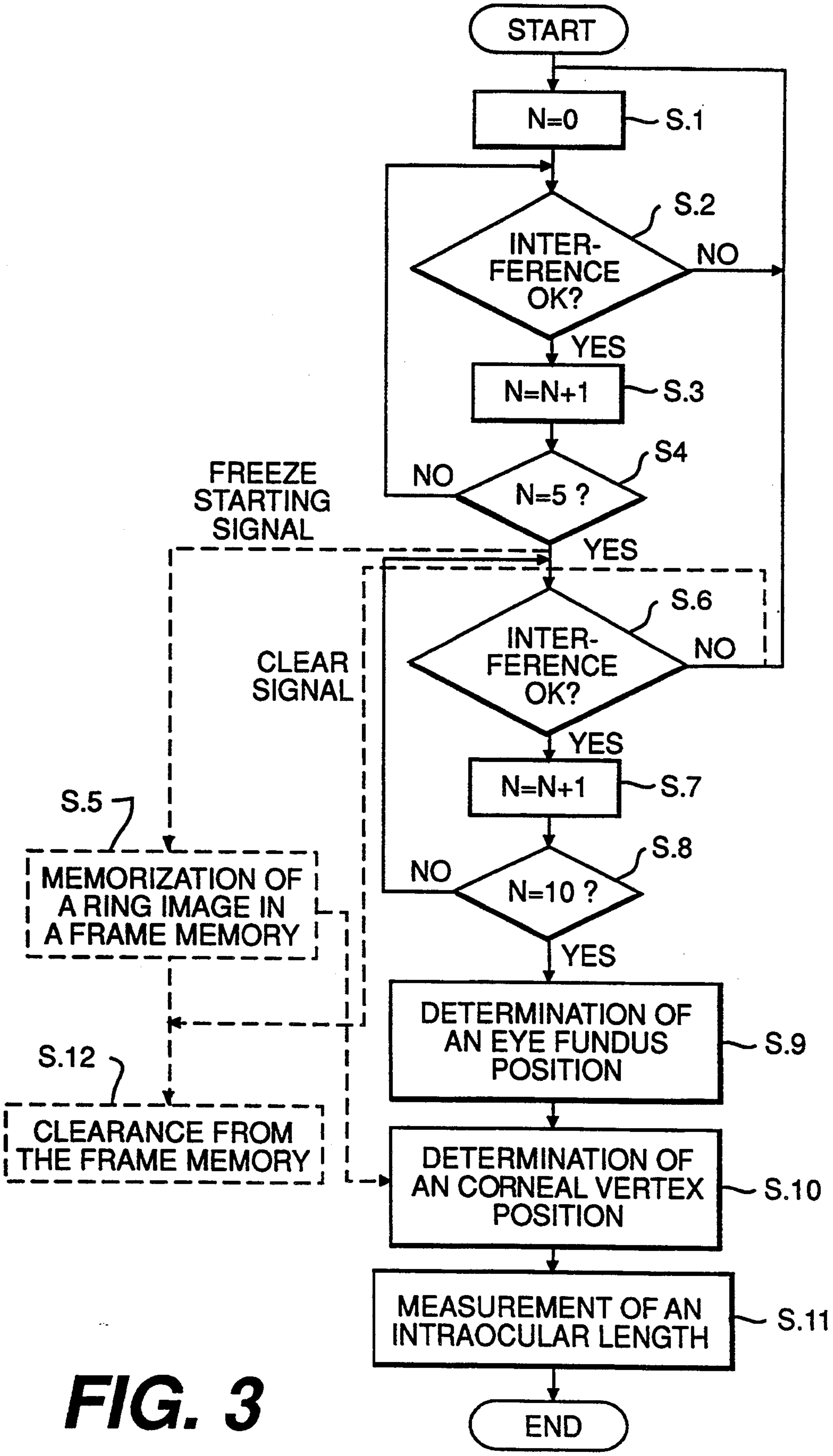
FIG. 3 is a flowchart showing a first embodiment of the intraocular length measuring instrument according to the invention.

The reflected light from the cornea 120 is guided to the half mirror 114 through the objective lens 104 and the dichroic mirror 115 and divided into two rays of light one of which proceeds to the first optical path 105 and the other to the second optical path 106. The reflected light of the first optical system 105 is once imaged as a ring-shaped aerial image 122 through a lens 113, and then imaged as a ring image i2 (see FIG. 2) on the two-dimensional image sensor 107 via a total reflection mirror 112, a lens 111, a diaphragm 110, a half mirror 109, and the image formation lens 108. The imaging power of this ring image i2 is 0.5 times in this embodiment. The reflected light of the second optical path 106 is reflected from the total reflection mirror 119, then once imaged as an aerial image 123 through the objective lens 104 and then imaged as a ring image i1 on the two-dimensional image sensor 107 through the total reflection mirror 118, the lens 117, the total reflection mirror 116, the diaphragm 124, the half mirror 109, and the image formation lens 108. The imaging power of this ring image i1 is set to be larger than that of the ring image i2. The diaphragm 110 is relayed to the neighborhood of the focusing position behind the objective lens 104 by the lenses 111, 113. The first optical system 100 is generally telecentric toward the object side. The numeral 125 denotes a conjugate image of the diaphragm 124. The diaphragm 124 is relayed to the forward of the eye 103 by the lens 117. A conjugate image (real image) 126 is formed in a position 25 mm to 50 mm away forward from the eye here.

The two-dimensional image sensor 107 outputs the data concerning the ring images to a frame memory 199. A description of timing to memorize the ring image data will be given hereinafter.

The signal processing circuit 200 serves as a circuit for determining the position of the surface of an intraocular object to be measured by sampling interference signals output by the photosensor 145, a means for reading the ring image data received by the two-dimensional image sensor 107 while the object surface position determining circuit is sampling the interference signals in order to memorize the ring image data in the frame memory 199 as a memory medium, and a circuit for determining the position of a corneal vertex 120P from the data concerning the ring images i1 and i2 memorized in the frame memory 199.

The signal processing circuit 200 first sets the count (N) of a counter, not shown, at 0 (N=0) in order to show how many times the detection data concerning a peak position are input (this step is referred to as S.1). A judgment as to whether the detection data have been input is then formed (S.2). If the detection data have not been input, the circuit 200 returns to S.1 and again performs the processing steps S.1 and S.2. If they have been input, the circuit 200 proceeds to the next step and adds 1 to the count The circuit 200 judges whether the count (N) is 5 (S.4). The circuit 200 repeats the processing steps S.2, S.3, S.4 until the count (N) becomes 5. As a result, the circuit 200 memorizes the detection data concerning such five peak positions as obtained by the above processing.

Next, the signal processing circuit 200 outputs a freeze starting signal to the frame memory 199. By this signal, the data concerning the ring images i1 and i2 are input in the frame memory 199 (S.5). The circuit 200 again judges whether the detection data concerning the peak position have been input (S.6). If the detection data have not been obtained, the circuit 200 returns to S.1 to reset the count (N) at 0 and again performs the processing steps S.1 to S.6. If they have been obtained, the circuit 200 proceeds to the next step and adds 1 to the count (N) (S.7). The circuit 200 judges whether the count (N) is 10 (S.8). The circuit 200 repeats the processing steps S.6 to S.8 until the count (N) becomes 10. As a result, the circuit 200 memorizes the detection data concerning such ten peak positions as obtained by the above processing. The circuit 200 determines the position of the eye fundus (S.9), the circuit 200 determines the position of the corneal vertex (S.10), and the circuit 200 calculates the intraocular length between the eye fundus and the corneal vertex (S.11). If the detection data concerning the peak position have not been obtained in the steps S.6 to S.8, the circuit 200 again returns to the step S.1 to sample the detection data concerning the peak positions and clears the ring image data concerning the ring images i1 and i2 from the frame memory 199 by a clear signal (S.12).

A confirmation of whether the position of the eye fundus has moved can be obtained by sampling the detection data concerning the peak position as mentioned above. Further, such sampling is applicable to a judgment on alignment.

(Embodiment 2)

Figure 4:
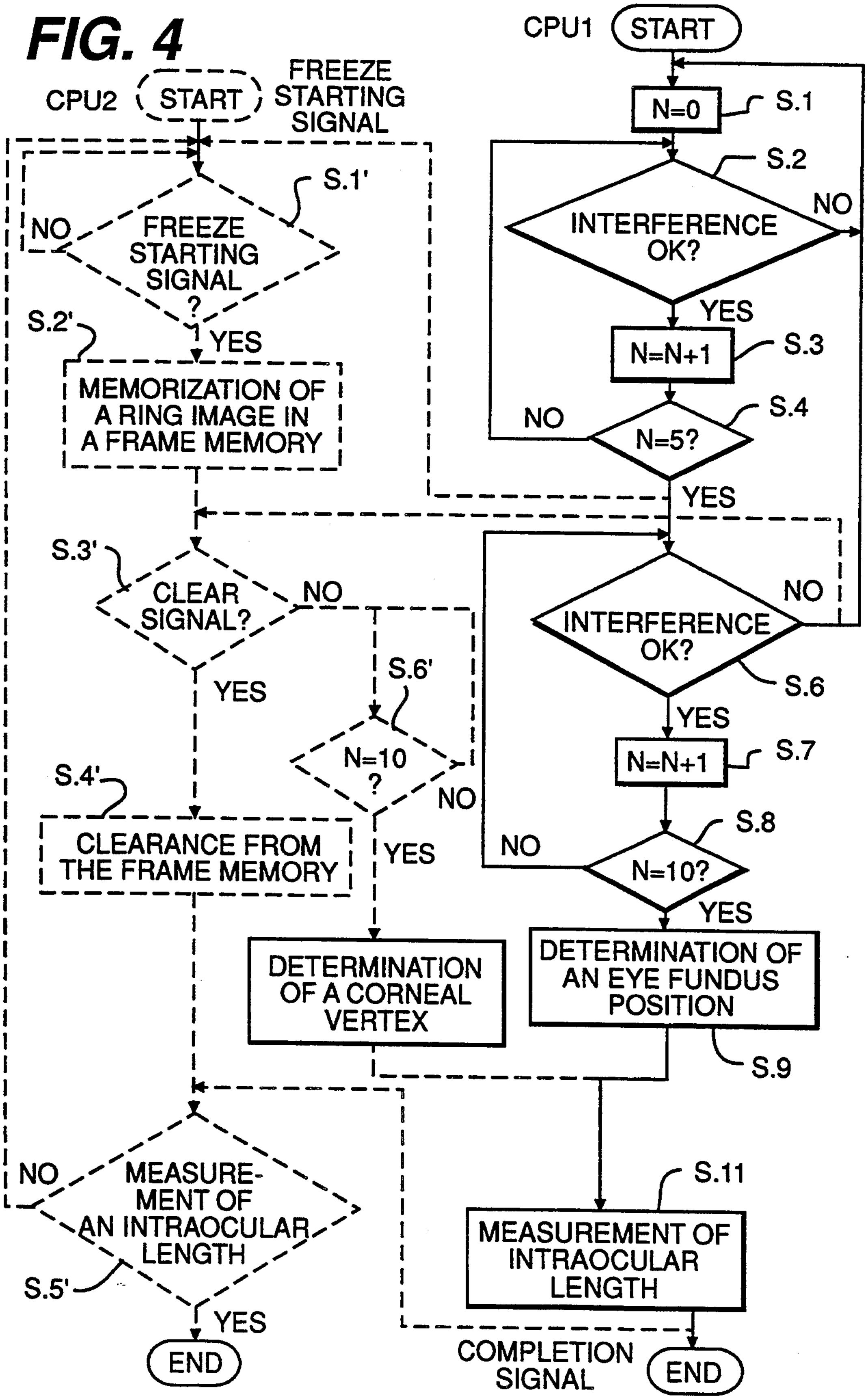
FIG. 4 is a flowchart showing a second embodiment of the intraocular length measuring instrument according to the invention.

FIG. 4 is a flowchart showing a second embodiment of an intraocular length measuring instrument according to the invention. In this embodiment, the signal processing circuit 200 includes two CPUs (Central Processing Unit), CPU1 and CPU2. CPU1 is used to sample the detection data concerning the peak positions. Since the processing flow in CPU1 is similar to that in the first embodiment, a detailed description thereof will be omitted. CPU2 judges whether a freeze starting signal is input at the same time as CPU1 starts to sample the detection data (S.1'). CPU2 repeats the processing of the step S.1' until it receives the freeze starting signal output by CPU1. When the freeze starting signal is input, the ring image data concerning the ring images i1 and i2 of the two-dimensional image sensor are input in the frame memory 199 and memorized therein (S.2'). CPU2 judges whether a clear signal has been input (S.3'). If the signal has been input, CPU2 clears the ring image data memorized in the frame memory 199 (S.4'). Next, CPU2 judges whether the intraocular length has been measured (S.5′). Since a judgment of "YES" formed in S.3′ means that the intraocular length has not yet been measured, CPU2 returns to S.1′ and repeats the processing of S.1′ to S.5′. When a judgment of "NO" is formed in S.3′, CPU2 judges whether the count (N) of the counter of CPU1 is 10 (S.6′). CPU2 keeps waiting until the count (N) becomes "10". When N=10, CPU2 determines the position of the corneal vertex from the ring image data memorized in the frame memory (S.7′). And then CPU2 outputs the data concerning the corneal vertex position to CPU1. CPU1 calculates the intraocular length from the data concerning the corneal vertex position and the eye fundus position (S.11). When the calculation of the intraocular length is completed, CPU1 outputs a completion signal to CPU2 and accordingly CPU1 and CPU2 come to the termination of all the processing at the same time.

According to the second embodiment, the processing time for the measurement of the intraocular length is shortening.

As another method, the corneal vertex position may be determined in such a way that the measuring instrument is provided with a plurality of frame memories 199. A plurality of ring image data memorized in the respective memories 199 and a plurality of data concerning the eye fundus can be averaged, and the corneal vertex position can be determined from the mean value.

(Embodiment 3)

Figure 5:
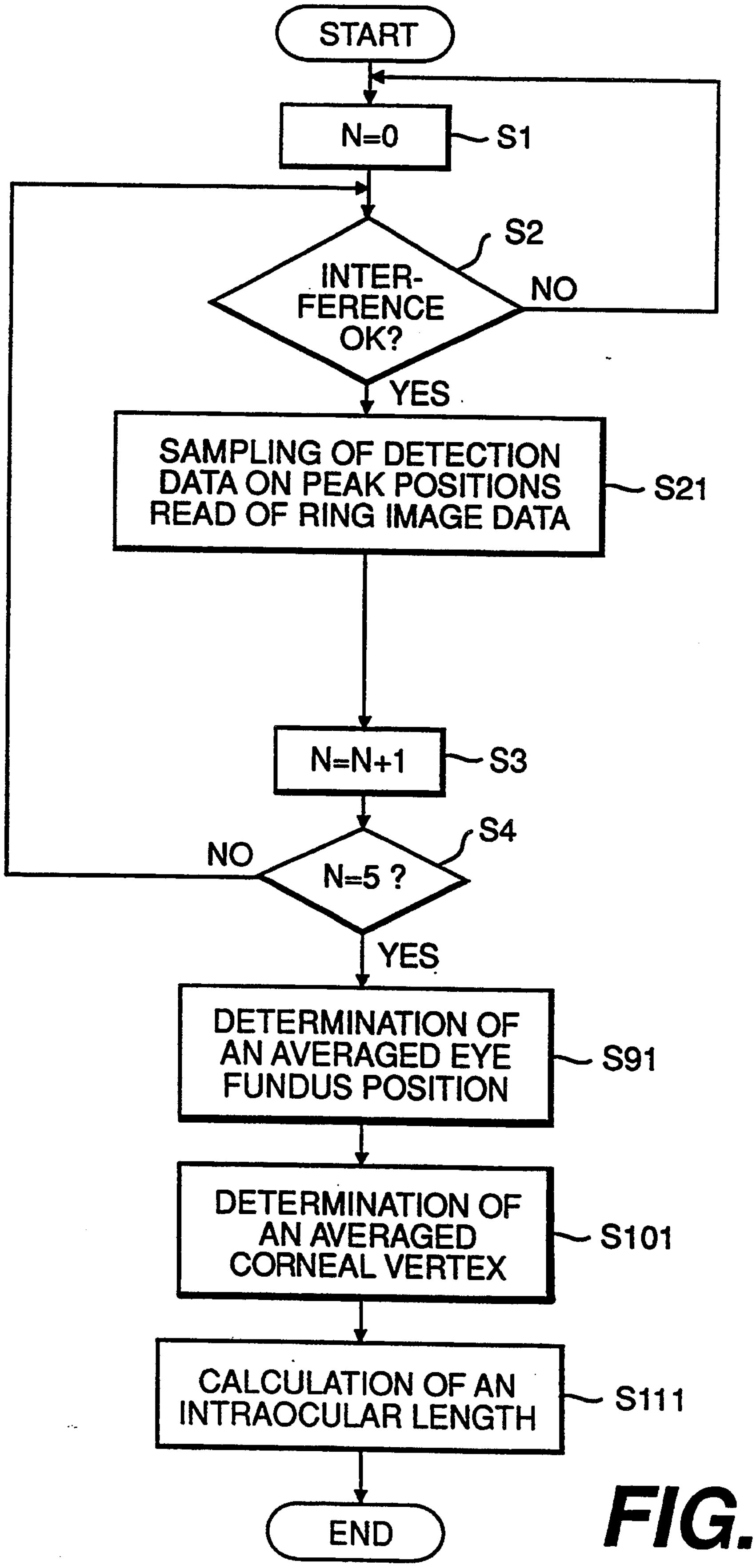
FIG. 5 is a flowchart showing a third embodiment of the intraocular length measuring instrument according to the invention.

FIG. 5 is a flowchart showing a third embodiment of an intraocular length measuring instrument according to the invention.

In this embodiment, the positions of the eye fundus and the corneal vertex are each determined by the same timing.

The same steps as those shown in the first embodiment will be described with the same numerals.

The signal processing circuit 200 sets the count (N) at "0". When an interference signal comes to a peak position, the circuit 200 samples and memorizes the detection data concerning the peak positions of the interference signals and simultaneously receives the ring image data (S.21). After that, the circuit 200 adds "1" to the count (N) (S.3) and repeats inputting the detection data concerning the peak positions and the corresponding ring image data until the count (N) becomes "5" (S.4). When the detection of the data concerning five peak positions is completed, the circuit 200 determines the corneal vertex position from the mean value of respective values obtained from the detection data concerning the five peak positions (S.101). The circuit 200 calculates an intraocular length from the corneal vertex position and the eye fundus position (S.111).

Another method may be adopted in which the count (N) in S.4 is set at "1" and the detection data concerning the peak positions of the interference signals are sampled and memorized one by one to input the ring image data.

According to the third embodiment, the measuring point of time of an intraocular object position can coincide with that of a corneal vertex position and therefore accuracy in measurement can be improved.

What is claimed is:

1. An intraocular length measuring instrument comprising:

a pattern image projecting and receiving optical system for projecting a pattern image onto a cornea of a subject's eye and receiving said pattern image into a two-dimensional image sensor;

an interferometric system for producing interference light in a way that measuring light is projected onto a surface of an intraocular object to be measured while reference light is projected onto a reference surface corresponding to said object surface and interference is caused between light reflected by said object surface and light reflected by said reference surface and causing a photosensor to receive said interference light and output an interference signal;

means for determining a position of said object surface by sampling said interference signal;

means for reading data concerning said pattern image received by said two-dimensional image sensor at any point of time of the duration of said sampling in order to memorize said pattern image data in a memory medium; and means for determining a position of a corneal vertex from said pattern image data memorized in said memory medium.

2. An intraocular length measuring instrument according to claim 1 wherein said reading means causes said memory medium to memorize said pattern image when about a half of all the number of times of sampling which said object surface position determining means performs are completed.

3. An intraocular length measuring instrument according to claim 1 wherein said reading means causes said memory medium to memorize said pattern image in accordance with said sampling and said corneal vertex position determining means determines a corneal vertex position from a plurality of pattern images memorized in said memory medium.

4. An intraocular length measuring instrument according to claim 1 wherein said pattern image projecting and receiving optical system projects a ring image onto said cornea and receives said ring image into said two-dimensional image sensor.

* * * * *